United States Patent
Jensen et al.

(10) Patent No.: US 8,785,446 B2
(45) Date of Patent: Jul. 22, 2014

(54) TREATING POST-SEIZURE PATIENTS

(75) Inventors: Frances E. Jensen, Boston, MA (US); Sanjay N. Rakhade, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 997 days.

(21) Appl. No.: 12/688,892

(22) Filed: Jan. 17, 2010

(65) Prior Publication Data

US 2010/0184650 A1    Jul. 22, 2010

Related U.S. Application Data

(60) Provisional application No. 61/145,532, filed on Jan. 17, 2009.

(51) Int. Cl.
*A61K 31/47* (2006.01)
*A61K 31/498* (2006.01)
*A61K 31/18* (2006.01)
*A61K 31/366* (2006.01)

(52) U.S. Cl.
CPC ............... *A61K 31/18* (2013.01); *A61K 31/366* (2013.01)
USPC ................... 514/252.12; 514/253.05; 514/183

(58) Field of Classification Search
CPC .............................. A61K 31/18; A61K 31/366
See application file for complete search history.

*Primary Examiner* — Robert C Hayes
(74) *Attorney, Agent, or Firm* — Fish & Richardson P.C.

(57) ABSTRACT

Patients are subject to a post-seizure treatment regime to separately inhibitor consecutive targets of an epileptogenic cascade comprising neurotransmitter receptor signaling, kinase/phosphatase activity, protein translation, and apoptosis or inflammation.

4 Claims, No Drawings

TREATING POST-SEIZURE PATIENTS

This application is a continuation of U.S. Ser. No. 61/145,532, filed Jan. 17, 2009, having the same title and inventors.

This work was supported by NIH Grant DP1OD003347 and NIH NICHHD P30 HD18655. The U.S. government may have rights in any patent issuing on this application.

BACKGROUND OF THE INVENTION

The field of the invention is treating post-seizure patients to interfere with epileptogenesis.

The highest incidence of seizures during lifetime is found in the neonatal period and neonatal seizures lead to a propensity for epilepsy and long-term cognitive deficits. Here we identify potential mechanisms that elucidate a critical role for AMPARs in epileptogenesis during this critical period in the developing brain. Using a rodent model of neonatal seizures, we have previously shown that administration of antagonists of the alpha-amino-3-hydroxy-5-methyl-4-isoxazole propionic acid subtype of glutamate receptors (AMPAR) during the 48 hours following seizures prevents long-term increases in seizure susceptibility and seizure-induced neuronal injury. Hypoxia-induced seizures in postnatal day (P) 10 rats induce rapid and reversible alterations in AMPAR signaling resembling changes previously implicated in models of synaptic potentiation in vitro. Hippocampal slices removed following hypoxic seizure exhibited potentiation of AMPAR-mediated synaptic currents, including an increase in the amplitude and frequency of spontaneous and miniature excitatory post-synaptic currents (EPSCs) as well as increased synaptic potency. This increased excitability was temporally associated with rapid increase in GluR1 S845/S831 and GluR2 S880 phosphorylation and increased activity of the protein kinases (including CamK II, PKA and PKC) that mediate the phosphorylation of the AMPARs. Post-seizure administration of AMPAR antagonists in vivo (including NBQX, topiramate, and GYKI-53773) attenuated the AMPAR potentiation, phosphorylation and kinase activation and prevented the concurrent increase in seizure susceptibility seen in vivo. Thus, potentiation of AMPAR-containing synapses is a reversible, early step in epileptogenesis that provides a novel therapeutic targets in the highly seizure-prone developing brain.

Aspects of this disclosure were published by the inventors in Rakhade et al., J Neurosci. 2008 Aug. 6; 28(32):7979-90.

SUMMARY OF THE INVENTION

In one aspect the invention provides, a therapeutic composition for treating a patient post-seizure, comprising a neurotransmitter receptor inhibitor and a kinase/phosphatase inhibitor.

In another aspect the invention provides a therapeutic composition for treating a patient post-seizure, comprising a neurotransmitter receptor inhibitor and a protein translation inhibitor.

In another aspect the invention provides a therapeutic composition for treating a patient post-seizure, comprising a neurotransmitter receptor inhibitor, a kinase/phosphatase inhibitor, and a protein translation inhibitor.

The invention encompasses all combinations of more particular embodiments of the invention:

further comprising an inhibitor of apoptosis or inflammation;

wherein each of the neurotransmitter receptor inhibitor and the kinase/phosphatase inhibitor is in a separately-contained unit dosage (e.g. separate capsules in a blister pack);

wherein each of the neurotransmitter receptor inhibitor and the protein translation inhibitor is in a separately-contained unit dosage (e.g. separate capsules in a blister pack);

wherein each of the neurotransmitter receptor inhibitor, the kinase/phosphatase inhibitor and the protein translation inhibitor is in a separately-contained unit dosage (e.g. separate capsules in a blister pack);

wherein the receptor is an AMPA receptor, NMDA receptor GABA receptor, chloride cotransporters, or metabatropic glutamate receptor;

wherein the kinase/phosphatase is a calmodulin kinase II (CamK II), protein kinase A (PKA), protein kinase C (PKC), MAP Kinase, Src kinase, ERK kinase or the phosphatase calcineurin;

wherein the kinase/phosphatase is calmodulin kinase II (CamK II), and the inhibitor is selected from: KN-62, W-7, HA-1004, HA-1077, and staurosporine;

wherein the kinase/phosphatase is protein kinase A (PKA), and the inhibitor is selected from: H-89, HA-1004, H-7, H-8, HA-100, PKI, and staurosporine;

wherein the kinase/phosphatase is protein kinase C (PKC), and the inhibitor is selected from:

competitive inhibitors for the PKC ATP-binding site, including staurosporine and its bisindolylmaleimide derivitives, Ro-31-7549, Ro-31-8220, Ro-31-8425, Ro-32-0432 and Sangivamycin;

drugs which interact with the PKC's regulatory domain by competing at the binding sites of diacylglycerol and phorbol esters, such as calphostin C, Safingol, D-erythro-Sphingosine;

drugs which target the catalytic domain of PKC, such as chelerythrine chloride, and Melittin;

drugs which inhibit PKC by covalently binding to PKC upon exposure to UV lights, such as dequalinium chloride;

drugs which specifically inhibit Ca-dependent PKC such as Gö6976, Gö6983, Gö7874 and other homologs, polymyxin B sulfate;

drugs comprising competitive peptides derived from PKC sequence; and

PKC inhibitors such as cardiotoxins, ellagic acid, HBDDE, 1-O-Hexadecyl-2-O-methyl-rac-glycerol, Hypercin, K-252, NGIC-I, Phloretin, piceatannol, and Tamoxifen citrate;

wherein the kinase/phosphatase is MAP kinase and the inhibitor is selected from: SB202190, and SB203580;

wherein the kinase/phosphatase is SRC kinase, and the inhibitor is selected from: PP1, PP2, Src Inhibitor No. 5, SU6656, staurosporine;

wherein the kinase/phosphatase is ERK kinase, and the inhibitor is selected from: PD 98059, SL327, olomoucine, 5-Iodotubercidin;

wherein the kinase/phosphatase is calcineurin and the inhibitor is selected from: tacrolimus, cyclosporine;

wherein the protein translation inhibitor is an mTOR inhibitors, such as rapamycin, CCl-779, RAD 001;

wherein patient is autistic and/or an infant.

In another aspect the invention provides a therapeutic method for treating a patient post-seizure with a comprising the steps: administering a neurotransmitter receptor inhibitor and a kinase/phosphatase inhibitor.

In another aspect the invention provides a therapeutic method for treating a patient post-seizure comprising the steps: administering a neurotransmitter receptor inhibitor and a protein translation inhibitor.

In another aspect the invention provides a therapeutic method for treating a patient post-seizure comprising the steps: administering a neurotransmitter receptor inhibitor, a kinase/phosphatase inhibitor and a protein translation inhibitor.

The invention encompasses all combinations of more particular embodiments of the invention:

further comprising administering an inhibitor of apoptosis or inflammation.

wherein the neurotransmitter receptor inhibitor and the kinase/phosphatase inhibitor are administered sequentially, wherein the neurotransmitter receptor inhibitor is administered first, within 24 (8, 4, 2) hours post-seizure, and the kinase/phosphatase inhibitor is administered second, within 48 (24, 12, 8) hours post-seizure;

wherein the neurotransmitter receptor inhibitor and the protein translation inhibitor are administered sequentially, wherein the neurotransmitter receptor inhibitor is administered first, within 24 hours post-seizure, and the protein translation inhibitor is administered second, within 96 (72, 48) hours post-seizure;

wherein the neurotransmitter receptor inhibitor, the kinase/phosphatase inhibitor, and the protein translation inhibitor are administered sequentially, wherein the neurotransmitter receptor inhibitor is administered first, within 24 hours post-seizure, the kinase/phosphatase inhibitor is administered second, within 48 hours post-seizure, and the protein translation inhibitor is administered third, within 96 hours post-seizure;

further comprising the step of diagnosing the patient as post seizure;

further comprising the step of diagnosing the patient as autistic; and further comprising the step of detecting a resultant neurotransmitter receptor, kinase/phosphatase or protein translation inhibition.

DETAILED DESCRIPTION OF SPECIFIC EMBODIMENTS OF THE INVENTION

The invention provides methods and compositions for treating a patient post-seizure. In one embodiment, the invention provides therapeutic compositions for treating a patient post-seizure, comprising separate inhibitors of multiple, distinct, consecutive targets of the epileptogenic cascade as described herein. In particular, the compositions comprise (a) a neurotransmitter receptor inhibitor and (b) a kinase/phosphatase inhibitor and/or a protein translation inhibitor, and in certain embodiments, (c) an inhibitor of apoptosis or inflammation.

The inhibitors are provided in therapeutically effective, synergistic amounts. By targeting distinct, sequential components of the epileptogenic cascade the inhibitors act synergistically, providing complementary efficacy. Hence, the inhibitors may be present and used in amounts suboptimal or subtherapeutic if used alone. Efficacy is anti-epileptogenic, comprising inhibiting epileptogenesis by inhibiting multiple, sequential epileptogenic cascade targets as described herein.

The distinct inhibitors may be admixed or copackaged; in a particular embodiment, each of the inhibitors is in a separately-contained unit dosage (e.g. separate capsules in a blister pack).

Target neurotransmitter receptors include an AMPA receptor, NMDA receptor GABA receptor, chloride cotransporters, or metabatropic glutamate receptor.

Target kinase/phosphatases include a calmodulin kinase II (CamK II), protein kinase A (PKA), protein kinase C (PKC), MAP Kinase, Src kinase, ERK kinase or the phosphatase calcineurin, and preferred inhibitors are tailored to the target kinase/phophatase. For example, in particular embodiments:

(a) the kinase/phosphatase is calmodulin kinase II (CamK II), and the inhibitor is selected from: KN-62, W-7, HA-1004, HA-1077, and staurosporine;

(b) the kinase/phosphatase is protein kinase A (PKA), and the inhibitor is selected from: H-89, HA-1004, H-7, H-8, HA-100, PKI, and staurosporine;

(c) the kinase/phosphatase is protein kinase C (PKC), and the inhibitor is selected from: competitive inhibitors for the PKC ATP-binding site, including staurosporine and its bisindolylmaleimide derivitives, Ro-31-7549, Ro-31-8220, Ro-31-8425, Ro-32-0432 and Sangivamycin;

drugs which interact with the PKC's regulatory domain by competing at the binding sites of diacylglycerol and phorbol esters, such as calphostin C, Safingol, D-erythro-Sphingosine;

drugs which target the catalytic domain of PKC, such as chelerythrine chloride, and Melittin;

drugs which inhibit PKC by covalently binding to PKC upon exposure to UV lights, such as dequalinium chloride;

drugs which specifically inhibit Ca-dependent PKC such as Gö6976, Gö6983, Gö7874 and other homologs, polymyxin B sulfate;

drugs comprising competitive peptides derived from PKC sequence; and

PKC inhibitors such as cardiotoxins, ellagic acid, HBDDE, 1-O-Hexadecyl-2-O-methyl-rac-glycerol, Hypercin, K-252, NGIC-I, Phloretin, piceatannol, and Tamoxifen citrate;

(d) the kinase/phosphatase is MAP kinase and the inhibitor is selected from: SB202190, and SB203580;

(e) the kinase/phosphatase is SRC kinase, and the inhibitor is selected from: PP1, PP2, Src Inhibitor No. 5, SU6656, staurosporine;

(f) the kinase/phosphatase is ERK kinase, and the inhibitor is selected from: PD 98059, SL327, olomoucine, 5-Iodotubercidin; and (g) the kinase/phosphatase is calcineurin and the inhibitor is selected from: tacrolimus, cyclosporine.

Alternative pharmacologically acceptable inhibitors effective in the disclosed methods are readily screened from the wide variety of PKC inhibitors known in the art (e.g Goekjian et al., 2001 Expert Opin Investig Drugs 10, 2117-40; Battaini, 2001, Pharmacolog Res 44, 353-61) using the disclosed in vivo protocols.

Exemplary suitable protein translation inhibitors are mTOR inhibitors, such as rapamycin, CCI-779, RAD 001, exemplary suitable inhibitors of apoptosis include epithalon, and exemplary suitable inhibitors of inflammation include corticosteroids and NSAIDs.

Neonatal seizures are associated with later neurodevelopmental and cognitive deficits including mental retardation, autism, and epilepsy, and it is estimated that up to 40% of cases of autism suffer from epilepsy or have a history of or seizures earlier in life. Accordingly, important target patients are infants, particularly neonates, and persons with a personal or family a history of seizure, mental retardation or autism.

The invention encompasses methods of treating a patient with the subject compositions to sequentially inhibit the target components of the epileptogenic cascade in their temporal order. Hence, the subject methods include treating a patient post-seizure comprising the steps: administering (a) a neurotransmitter receptor inhibitor and (b) a kinase/phosphatase inhibitor, and/or a protein translation inhibitor, and optionally (c) an inhibitor of apoptosis or inflammation.

The inhibitors are administered in conventional form and manner tailored to the inhibitor and patient, and may be administered orally, by intravenous (i.v.) bolus, by i.v. infusion, subcutaneously, intramuscularly, ocularly (intraocularly, periocularly, retrobulbarly, intravitreally, subconjunctivally, topically, by subtenon administration, etc.), intracranially, intraperitoneally, intraventricularly, intranasally, intrathecally, by epidural, etc. Depending on the intended route of delivery, the inhibitors may be administered in one or more dosage form(s).

The subject treatment regimes are tailored in time and sequence to the time course of the epileptogenic cascade as initiated by hypoxia, hypoxia-associate seizure or other form of status epilepticus. Indications include post-asphyxia, post-respiratory distress, post-hypotension, oxygen deficit to the brain or focal area of the brain as cause, for example, by stroke, TBI, infection etc., other forms of status epilepticus from metabolic of structural origins (e.g. tumor, hydrocephalus, cortical dysplasia, tuberous sclerosis, and infantile spasms, particular at 1-18 months. For example, in particular embodiments:

(i) the neurotransmitter receptor inhibitor and the kinase/phosphatase inhibitor are administered sequentially, wherein the neurotransmitter receptor inhibitor is administered first, preferably within 24 (or 8, or 4, or 2 or 1) hours post-seizure, and the kinase/phosphatase inhibitor is administered second, preferably within 48 (or 24, or 12, or 8 or 4 or 2) hours post-seizure;

(ii) the neurotransmitter receptor inhibitor and the protein translation inhibitor are administered sequentially, wherein the neurotransmitter receptor inhibitor is administered first, preferably within 24 hours post-seizure, and the protein translation inhibitor is administered second, preferably within 96 (or 72, or 48, or 24, or 12, or 8, or 4) hours post-seizure; or (iii) the neurotransmitter receptor inhibitor, the kinase/phosphatase inhibitor, and the protein translation inhibitor are administered sequentially, wherein the neurotransmitter receptor inhibitor is administered first, preferably within 24 (or 8, or 4, or 2 or 1) hours post-seizure, the kinase/phosphatase inhibitor is administered second, preferably within 48 (or 24, or 12, or 8, or 4, or 2) hours post-seizure, and the protein translation inhibitor is administered third, preferably within 96 (or 72, or 48, or 24, or 12, or 8, or 4) hours post-seizure.

The administration schedule may further comprise an inhibitor of inflammation or apoptosis, preferably administered before, during or after the protein translation inhibitor, preferably fourth, preferably within 96 (or 72, or 48, or 24, or 12, or 8, or 4) hours post-seizure.

The subject methods may comprise the antecedent step of diagnosing the patient as in need of the subject treatment, such as determining that the patient is post seizure, particularly post-seizure and suffering from (resultant) autism or mental retardation. In particular embodiments, the patient is determined to have a history of seizure wherein the seizure is hypoxia-associated, refractory to conventional treatment, lasting longer than 30 minutes, or recurrent.

The subject methods may comprise the subsequent step of detecting a resultant neurotransmitter receptor, kinase/phosphatase or protein translation inhibition, or other indication of interference with epileptogenesis or efficacy of the treatment, such as normalization of EEG measures, reduction in seizure behavior or cognitive impairment or deficit, e.g. neuropsychiatric metrics, such as Bayley score.

In particular embodiments, patients are monitored with live 24/7 EEG while under treatment to evaluate efficacy on seizure frequency, particularly as compared to a normative standard, or a control, such as vehicle or placebo-treated patients, and then receive follow up to evaluate seizure recurrence rates, neuropsychiatric outcome etc. In particular embodiments, MRI is monitored acutely, particularly in cases evidencing a level of associated and/or causative brain injury. The subject treatments can be used to suppress such recurrent seizures and reduce the likelihood or severity of them worsening these lesions.

The subject treatments can provide an adjunctive therapy, preferably with an effective AED or AMPAR antagonist for anticonvulsant treatment and seizure suppression. The kinase/phosphatases inhibitors can also be effective at suppressing prolonged seizure activity, as this pathway gets activated within minutes of the start of a seizure so this treatment can begin to shorten the seizure once it crosses the blood-brain barrier.

EXAMPLES

Early Alterations of AMPA Receptors Mediate Synaptic Potentiation Induced by Neonatal Seizures The incidence of epilepsy is highest in the first year of life and peaks in the neonatal period (Volpe, 2001). Hypoxic encephalopathy in term infants is the most common cause of neonatal seizures, resulting in severe long-term consequences (Volpe, 2001; Jensen, 2006). The neonatal brain exhibits a predominance of excitatory neurotransmission over inhibition due to developmental regulation of expression of neurotransmitter receptors, ion channels, and transporters (Silverstein and Jensen, 2007). Early-life seizures cause permanent functional alterations in neuronal networks and render the brain susceptible to later epilepsy and cognitive deficits (Ben Ari and Holmes, 2006; Silverstein and Jensen, 2007). Furthermore, current anticonvulsants are largely ineffective in neonatal seizure (Sankar and Painter, 2005), emphasizing the need for better understanding underlying mechanisms.

Animal model data suggest that early-life seizures result in long-term hyperexcitability and long-lasting sequelae (Chen et al., 1999; Silverstein and Jensen, 2007; Sogawa et al., 2001), and even a single neonatal seizure may permanently alter glutamatergic synapses (Cornejo et al., 2007). However, the specific targets and mechanisms that mediate changes in synaptic strength in the acute period following seizures remain largely elusive.

We established a model of hypoxic seizures in postnatal day (P) 10 rats, resulting in long-term increases in seizure susceptibility and decreased neurobehavioral performance (Jensen et al., 1992; Mikati et al., 2005). A role for AMPARs in these changes was indicated when treatment with AMPAR antagonists, but not NMDA receptor antagonists or GABA agonists, preferentially suppressed seizures and their long term consequences. Administration of AMPAR antagonists in the first 48 hours following seizures attenuated long-term increases in seizure susceptibility and seizure-induced neuronal injury in hippocampus (Koh et al., 2004), suggesting that acute alterations in AMPARs in the 48 hours following neonatal seizures may play a critical role in epileptogenesis. Previous studies with depth electrode recordings confirmed the presence of ictal activity in the hippocampus during hypoxia (Jensen et al., 1998). In addition, hypoxia-induced seizures at P10 have been reported to induce subacute and specific decrease in AMPAR GluR2 and calcineurin-mediated decrease in GABA-ergic transmission, as well as lead to potentiation of hippocampal network hyperexcitability in vitro (Sanchez et al., 2001; Sanchez et al., 2005).

The period of greatest susceptibility to early-life seizures is coincident with the critical period of brain development, characterized by maximal synaptic density (Rakic et al., 1989), as well as the highest neuronal expression of $Ca^{2+}$ permeable, GluR2 subunit-deficient, AMPARs (Tabs et al., 2006a; Kumar et al., 2002). Activity-dependent phosphorylation/dephosphorylation of intracellular carboxy-terminal sites on the AMPAR subunits GluR1 and GluR2 regulates their synaptic trafficking and functional properties, as described in long-term potentiation (LTP) and long-term depression (LTD) (Barria et al., 1997; Seidenman et al., 2003). For example, phosphorylation of GluR1 S831 and GluR1 S845 regulates both open channel conductance as well as synaptic incorporation of the receptor in the early phase of LTP (Lee et al., 2000; Malinow and Malenka, 2002). Similarly, phosphorylation of the GluR2 subunit at S880 modulates its interaction with glutamate receptor-interacting protein (GRIP) and results in receptor endocytosis (Wyszynski et al., 1999). We hypothesized that similar dynamic mechanisms involving AMPARs may play an important role in epileptogenesis, given the efficacy of early post-seizure AMPAR antagonist treatment in our seizure model.

Consistent with our hypothesis, we observed that hypoxia-induced seizures in the immature rat resulted in a rapid increase in AMPAR-mediated synaptic currents, an increase in GluR1 and GluR2 subunit phosphorylation, and a transient increase in the activity of CaMKII, PKA and PKC. Furthermore, administration of AMPAR antagonists immediately following hypoxic seizures attenuated these alterations and the concurrent enhanced seizure susceptibility.

Early Enhancement of AMPAR-Mediated Spontaneous EPSCs Following Hypoxia-Induced Seizures Neonatal seizures have been described to enhance the excitability of hippocampal networks as well as cause alterations in long-term network excitability (Jensen et al., 1991; Sanchez et al., 2001; Silverstein and Jensen, 2007; Cornejo et al., 2007), but their acute effects on AMPAR function have not been examined. We compared spontaneous (s) and miniature (m) AMPAR-mediated excitatory postsynaptic currents (EPSCs) in CA1 pyramidal neurons in P10 rat pup hippocampal slices removed 1 hour after hypoxia-induced seizures (hypoxic seizures) and normoxic control rat pups. Slices from pups with hypoxic seizures showed significantly larger amplitude sEPSCs recorded in CA1 neurons compared to slices from normoxic control pups, and these events occurred at significantly higher frequency as compared to normoxic controls. Consistent with the enhanced sensitivity of sEPSCs, post-seizure AMPAR-mediated mEPSCs in CA1 neurons showed significantly increased amplitude and frequency compared to normoxic controls.

To elucidate whether modifications of postsynaptic AMPARs contributed to the increase in sEPSCs following hypoxic seizures, we compared minimally evoked AMPAR-mediated unitary EPSCs in single fibers from CA1 pyramidal neurons in slices removed 1 hour after hypoxic seizures with CA1 neurons from normoxic control rats. The distribution of successful eEPSC events was shifted to larger amplitudes in the slices removed after seizures, and neurons in these slices exhibited a significant increase in synaptic potency compared to slices from normoxic controls. In addition, no significant change of paired-pulse facilitation was observed between the hippocampal slices from animals experiencing hypoxic seizures and normoxic animals at this age (Supplementary figure S2), similar to our observations with extracellular recordings in CA1 neurons (Jensen et al., 1998). These data suggested to us that hyperexcitability observed following neonatal seizures may result from changes in activation of post-synaptic neurotransmitter receptors, and this may contribute to the resultant epileptogenesis.

Increased AMPAR GluR1 Subunit Phosphorylation Following Early-Life Seizure

Together the electrophysiological data suggest that hypoxia-induced seizures in the immature rat resulted in increased AMPAR-mediated excitability of CA1 hippocampal neurons. The strength of synaptic transmission in intact neuronal networks, such as in LTP, can be regulated by altered AMPAR function mediated by phosphorylation of GluR1 S831 and GluR1 S845 (Barria et al., 1997; Lee et al., 2000; Lee et al., 2003). We observed an increase in the phosphorylation of GluR1 S831 as early as 1 hour after hypoxic seizures compared to normoxic control littermates. The phosphorylation of GluR1 S831 was observed to be persistently increased at 6, 12 and 24 hours post-hypoxia before returning to baseline, with the maximal increase observed at 24 hours following hypoxic seizures. We similarly observed increased GluR1 S845 subunit phosphorylation as early as 1 hour following hypoxic seizures. Phosphorylation of GluR1 S845 remained persistently increased at 6, 12 and 24 hours following hypoxia-induced seizures, with the maximal increase observed at 24 hours post-hypoxic seizures. Thus, the seizure-induced increases in phosphorylation of GluR1 subunit sites were concurrent with the enhancement of AMPAR-mediated synaptic currents.

Rapid Seizure-Induced Increase in Inward Rectification of Ampar-Mediated EPSCs Along with Increased GluR2 Subunit Phosphorylation The age window around P10-12 is characterized by a relative preponderance of $Ca^{2+}$ permeable AMPARs in hippocampal and neocortical neurons resulting from a developmentally regulated decrease in GluR2 subunit expression (Sanchez et al., 2001; Durand and Zukin, 1993; Talos et al., 2006b; Kumar et al., 2002). Additionally, hypoxic seizures have been previously associated with a decrease in the expression of GluR2 mRNA and protein 48 hours following the induction of seizures (Sanchez et al., 2001). However the acute alterations in the phosphorylation and function of GluR-2 lacking AMPARs following hypoxic seizures have not been well-characterized. We characterized the GluR2 deficiency of synaptic AMPARs by determining the rectification index of eEPSCs in slices removed at 1 hour after in vivo seizures in the P10 pup, and found that the rectification index was significantly increased in slices from animals after hypoxic seizures compared with normoxic controls. Furthermore, bath application of PhTX-433 (10 μM), a specific antagonist for GluR2-lacking AMPARs, blocked the majority of eEPSCs in CA1 pyramidal neurons post-hypoxia as compared to eEPSCs in CA1 neurons from normoxic controls confirming the presence of synaptic GluR2-deficient AMPARs following seizures. Expression of inwardly rectifying AMPAR-mediated currents can result from an increase in phosphorylation of GluR2 S880 and resultant trafficking of the GluR2 subunit out of the synaptic membrane (Chung et al., 2000; Kim et al., 2001; Seidenman et al., 2003). Indeed, GluR2 S880 phosphorylation was increased in the hippocampus of rats experiencing hypoxic seizures as compared to normoxic litter mates, maximal at 12 hours post hypoxia. This seizure-induced phosphorylation of GluR2 S880 may contribute to the subacute changes in GluR2 expression reported previously (Sanchez et al., 2001), as well as increased inward rectification of EPSPs reported above.

Increased Activity of Protein Kinase PKA, PKC and CaMKII

Protein kinase A (PKA) and calcium calmodulin dependent kinase II (CaMKII) mediates the phosphorylation of GluR1 S845 and protein kinase C (PKC) is involved in the phosphorylation of both GluR1 S831 (Kameyama et al., 1998; Mammen et al., 1997) and GluR2 S880 (Seidenman et al., 2003). ELISA assays demonstrated a significant increase in PKA activity at 1 hour following hypoxia-induced seizures, returning to baseline levels observed in normoxic controls by 6 hours. Similarly, CaMKII activity increased at 1 hour post-seizures before returning to baseline levels at 6 hours post-hypoxia. In contrast to PKA and CaMKII, the increases in PKC activity were more prolonged: PKC activity rapidly increased in at 1 hour post-hypoxia, was maximally increased at 6 hours post hypoxia, and returned to baseline levels by 12 hours following hypoxic seizures. The rapid seizure-induced activation of these protein kinases are occurring coincident with the alterations in phosphorylation state of their known substrates, GluR1 S831, GluR1 S845, and GluR2 S880.

AMPAR Antagonists Attenuate Seizure-Induced Phosphorylation and Functional Alterations in AMPARs and Kinase Activation We have demonstrated rapid and transient increase in phosphorylation of AMPARs following seizures, coincident with altered receptor function, and these changes are occurring in the time window in which we previously have reported protective efficacy of post seizure treatment with AMPAR antagonists. To determine whether seizure-induced activation of AMPAR plays a critical role in the alterations in EPSCs and subunits reported here, we examined whether pharmacologic inhibition of AMPARs in vivo following hypoxic seizures leads to a decrease in the activity of $Ca^{2+}$ dependent protein kinases and GluR1 subunit phosphorylation state. Notably, at P10, hippocampal and pyramidal neurons express $Ca^{2+}$ permeable AMPARs (Sanchez et al., 2001; Kumar et al., 2002). Within 30 minutes after hypoxic seizures, rats were treated with a single dose of systemically administered AMPAR antagonists NBQX (20 mg/kg), topiramate (30 mg/kg) or GYKI-53773 (7.5 mg/kg), and compared to vehicle-treated (0.1 ml PBS) hypoxic controls and normoxic littermates. These treatment doses are the same as the treatment paradigm in which we previously observed an attenuation of long-term epileptogenic changes (Koh et al., 2004). NBQX can block both AMPA and KA receptors but preferentially blocks AMPARs, topiramate is a clinically available anticonvulsant demonstrated to have AMPAR antagonist properties but has actions at other voltage and ligand gated ion channels, and GYKI-53773 is currently in clinical trials and is a specific noncompetitive AMPAR antagonist. Importantly, blockade of AMPAR-mediated neurotransmission is the common mechanistic feature of these three structurally unrelated compounds and may represent the potential mode of mediating alterations. While GluR1 S831 phosphorylation was increased at 12 hours following vehicle treatment after hypoxic seizures, consistent with the increased phosphorylation observed previously, this increase was significantly reduced to baseline normoxia levels following post-treatment with NBQX, topiramate or GYKI-53773. Similarly, the increase in phosphorylation of GluR1 S845 observed at 12 hours following hypoxia-induced seizures was significantly reduced to baseline normoxia levels following post-treatment with NBQX, topiramate or GYKI-53773 compared to vehicle treatment following hypoxic seizures.

These treatment paradigms also resulted in a significant attenuation of the seizure-induced activity increases of CaMKII, PKA, and PKC. The activity of CaMKII at 1 hour following hypoxic seizures was reduced to near baseline levels observed in normoxic animals, following in vivo administration of NBQX, topiramate and GYKI-53773 versus vehicle treatment following hypoxic seizures. Similarly, seizure-induced PKA activation at 1 hour following hypoxic seizures was reduced significantly following administration of NBQX and topiramate versus vehicle treatment following hypoxic seizures. Unlike the assessment of activity at 1 hour for PKA and CaMKII, we assayed PKC activity at 6 hours post-hypoxic seizures because this was when it was maximally increased. The seizure-induced increase in PKC activity was significantly reduced following administration of NBQX and GYKI-53773 versus vehicle treatment following hypoxic seizures compared to normoxic controls. Similar results were observed on assaying PKC activity at 3 hours post hypoxia following administration of AMPAR antagonists/ Thus, our results indicate that the attenuation in the activity of protein kinases PKA, CaMK II and PKC at early time periods is associated with a temporally relevant decrease in the phosphorylation of their substrate sites on the AMPARs, e.g. GluR1 S831 and S845.

AMPAR Antagonist Post Treatment Attenuates Enhanced AMPAR-Mediated sEPSCs Following Seizures Given the observation that treatment with AMPAR antagonists immediately following seizures suppressed seizure-induced kinase activation and subunit phosphorylation, we next determined whether the treatment also attenuated the alterations in AMPAR sEPSCs. Following hypoxic seizures, NBQX, topiramate or GYKI-53773 were administered to the rat pups experiencing hypoxic seizures and hippocampal slices were prepared 1 hour after administration of AMPAR antagonists. The in vivo administration of AMPAR antagonists significantly decreased the sEPSCs in amplitude observed in the ex vivo hippocampal slices as shown in the cumulative distribution histogram. sEPSC amplitude was significantly attenuated in hippocampal slices from animals post-hypoxic seizure administration of NBQX, topiramate and GYKI-53773, compared to vehicle treatment. Similarly, we observed an attenuation of sEPSC frequency following administration of NBQX, topiramate and GYKI-53773 compared to vehicle treatment post hypoxic seizures.

Increased Seizure Susceptibility Observed after Hypoxic Seizures is Reversed by AMPAR Antagonist Treatment Given that we showed that AMPAR antagonist post seizure treatment suppressed seizure induced alterations in AMPAR subunits and function, we next evaluated whether in the present model there was an associated in vivo effect on later seizure susceptibility. We have previously reported that enhanced hippocampal excitability observed in rat pups following hypoxia-induced seizures is reflected in the increased susceptibility to KA-induced seizures in these animals at both short (72-96 h) and long (40+ days) intervals following the initial seizures at P10 (Koh et al., 2004). KA (2 mg/kg i.p.) was administered 3 days after hypoxic seizures at P10, and the latency to onset of both the first behavioral seizure and forelimb clonus was observed to be significantly shorter and seizure severity higher in animals with prior hypoxic seizures compared to normoxic littermate controls. The administration of the AMPAR antagonist NBQX (20 mg/kg i.p.) following hypoxic seizures significantly attenuated the enhanced seizure susceptibility at P13. The latency to seizures in NBQX-treated animals was significantly longer compared to vehicle treated hypoxic controls. In addition, the maximal seizure severity was significantly lower in the NBQX-treated group as compared to vehicle-treated pups that had previously experienced hypoxic seizures.

Increased Seizure Susceptibility Observed after Hypoxic Seizures is Synergistically Reversed by Sequentially Inhibiting Multiple Targets of Epileptogenic Cascade.

We have demonstrated that treatment with inhibitors of kinase/phosphateses of the epileptogenic cascade following seizures can block the enhanced synaptic excitability and also the alterations in phosphorylation state at glutamate and GABA receptor subunits implicating kinase and phosphatase activation as early steps in epileptogenesis, and revealing a reversible step in the process of epileptogenesis. In conjunction with our work showing that AMPAR antagonist post seizure treatment suppressed seizure induced alterations in AMPAR subunits and function, and suppressed later seizure susceptibility, we next show that increased seizure susceptibility observed after hypoxic seizures is synergistically reversed by sequentially inhibiting multiple targets of epileptogenic cascade using coordinated treatment regimes.

In treatment groups A1-A7, AMPAR antagonist NBQX (20 mg/kg i.p.) and kinase/phosphatase inhibitor KN-62, H-89, Ro-31-7549, SB202190, PP1, PD 98059, or tacrolimus (5 mg/kg i.p.) are administered 1 and 2 days, respectively, after hypoxic seizures at P10; in treatment group B, AMPAR antagonist NBQX (20 mg/kg i.p.) and rapamycin (2 mg/kg i.p.) are administered 1 and 3 days, respectively, after hypoxic seizures at P10; in treatment groups C1-C7, AMPAR antagonist NBQX (20 mg/kg i.p.), kinase/phosphatase inhibitor KN-62, H-89, Ro-31-7549, SB202190, PP1, PD 98059, or tacrolimus (5 mg/kg i.p.) and rapamycin (2 mg/kg i.p.) are administered 1, 2 and 3 days, respectively, after hypoxic seizures at P10; and in treatment group D, AMPAR antagonist NBQX (20 mg/kg i.p.), kinase/phosphatase inhibitor KN-62 (5 mg/kg i.p.), rapamycin (2 mg/kg i.p.) and ibuprofen (5 mg/kg i.p.) are administered 1, 2, 3 and 4 days, respectively, after hypoxic seizures at P10.

In each of these treatment regime following hypoxic seizures significantly attenuates the enhanced seizure susceptibility at P15—even more so than the NBQX-only treatment. The latency to seizures in regime-treated animals is significantly longer compared to vehicle treated hypoxic controls, and even longer than in the NBQX-only treated animals. In addition, the maximal seizure severity is significantly lower in each of the regime-treatment groups as compared to vehicle-treated pups (and even the NBQX-treated pups) that had previously experienced hypoxic seizures.

Subsequent work using the same pharmaceutical series: two-component series A and B (AMPAR antagonist+kinase/phosphatase inhibitor or rapamycin), three-component series C (AMPAR antagonist+kinase/phosphatase inhibitor+rapamycin), and four component series D (AMPAR antagonist+kinase/phosphatase inhibitor+rapamycin+NSAID) over varying administration schedules demonstrate similarly synergistic inhibition of epileptogenesis and seizure susceptibility:

Series A8: (i) NBQX (20 mg/kg i.p.) at 5 min; KN-62 (5 mg/kg i.p.) at 1 hr; (ii) NBQX (20 mg/kg i.p.) at 5 min; KN-62 (5 mg/kg i.p.) at 12 hr; (iii) NBQX (20 mg/kg i.p.) at 1 hr; KN-62 (5 mg/kg i.p.) at 12;

Series A9: (i) topiramate (30 mg/kg i.p.) at 5 min; Tamoxifen citrate (2 mg/kg i.p.) at 1 hr; (ii) topiramate (30 mg/kg i.p.) at 5 min; Tamoxifen citrate (2 mg/kg i.p.) at 12 hr; (iii) topiramate (30 mg/kg i.p.) at 1 hr; Tamoxifen citrate (2 mg/kg i.p.) at 12 hr;

Series B2: (i) NBQX (20 mg/kg i.p.) at 5 min; rapamycin (2 mg/kg i.p.) at 4 hr; (ii) NBQX (20 mg/kg i.p.) at 5 min; rapamycin (2 mg/kg i.p.) at 24 hr; (iii) NBQX (20 mg/kg i.p.) at 1 hr; rapamycin (2 mg/kg i.p.) at 48 hr;

Series B3: (i) topiramate (30 mg/kg i.p.) at 5 min; rapamycin (2 mg/kg i.p.) at 4 hr; (ii) topiramate (30 mg/kg i.p.) at 5 min; rapamycin (2 mg/kg i.p.) at 24 hr; (iii) topiramate (30 mg/kg i.p.) at 1 hr; rapamycin (2 mg/kg i.p.) at 48 hr;

Series C8: (i) NBQX (20 mg/kg i.p.) at 5 min; KN-62 (5 mg/kg i.p.) at 1 hr; rapamycin (2 mg/kg i.p.) at 4 hr; (ii) NBQX (20 mg/kg i.p.) at 5 min; KN-62 (5 mg/kg i.p.) at 12 hr; rapamycin (2 mg/kg i.p.) at 24 hr; (iii) NBQX (20 mg/kg i.p.) at 1 hr; KN-62 (5 mg/kg i.p.) at 12; rapamycin (2 mg/kg i.p.) at 48 hr;

Series C9: (i) topiramate (30 mg/kg i.p.) at 5 min; Tamoxifen citrate (2 mg/kg i.p.) at 1 hr; rapamycin (2 mg/kg i.p.) at 4 hr; (ii) topiramate (30 mg/kg i.p.) at 5 min; Tamoxifen citrate (2 mg/kg i.p.) at 12 hr; rapamycin (2 mg/kg i.p.) at 24 hr; (iii) topiramate (30 mg/kg i.p.) at 1 hr; Tamoxifen citrate (2 mg/kg i.p.) at 12 hr; rapamycin (2 mg/kg i.p.) at 48 hr;

Series D2: (i) NBQX (20 mg/kg i.p.) at 5 min; KN-62 (5 mg/kg i.p.) at 1 hr; rapamycin (2 mg/kg i.p.) at 4 hr; ibuprofen (5 mg/kg i.p.) at 12 hr; (ii) NBQX (20 mg/kg i.p.) at 5 min; KN-62 (5 mg/kg i.p.) at 12 hr; rapamycin (2 mg/kg i.p.) at 24 hr; ibuprofen (5 mg/kg i.p.) at 24 hr; (iii) NBQX (20 mg/kg i.p.) at 1 hr; KN-62 (5 mg/kg i.p.) at 12; rapamycin (2 mg/kg i.p.) at 48 hr; ibuprofen (5 mg/kg i.p.) at 48 hr;

Series D3: (i) topiramate (30 mg/kg i.p.) at 5 min; Tamoxifen citrate (2 mg/kg i.p.) at 1 hr; rapamycin (2 mg/kg i.p.) at 4 hr; prednisone (1 mg/kg i.p.) at 12 hr; (ii) topiramate (30 mg/kg i.p.) at 5 min; Tamoxifen citrate (2 mg/kg i.p.) at 12 hr; rapamycin (2 mg/kg i.p.) at 24 hr; prednisone (1 mg/kg i.p.) at 24 hr; (iii) topiramate (30 mg/kg i.p.) at 1 hr; Tamoxifen citrate (2 mg/kg i.p.) at 12 hr; rapamycin (2 mg/kg i.p.) at 48 hr; prednisone (1 mg/kg i.p.) at 48 hr.

Analysis

We observed that early-life seizures lead to a rapid enhancement of AMPAR-mediated synaptic currents and this was associated with rapid increases in AMPAR phosphorylation at GluR1 S831, GluR1 S845 and GluR2 S880 sites, in addition to activation of CaMKII, PKA, and PKC. Systemic administration of AMPAR antagonists immediately following seizures attenuated the early increase in AMPAR function and phosphorylation. Furthermore, AMPAR antagonist administration in P10 rats following early-life seizures also attenuated the increased seizure susceptibility observed in vehicle-treated pups. These results indicate that the potentiation of AMPAR-containing synapses is a reversible, early step in epileptogenesis that offers a novel therapeutic target in the highly seizure-prone developing brain.

Post-Translational Modifications of AMPARs Mediate Hippocampal Hyperexcitability Following Seizures in the Immature Brain A central and novel finding of our work is that seizures cause rapid alterations in AMPAR subunit composition and function in the developing brain. Enhanced synaptic AMPAR strength may be an important component of the acute and long-term seizure-induced hyperexcitability that constitutes epileptogenesis. Our work showed that both sEPSCs and mEPSCs were increased in amplitude and frequency in CA1 neurons from hippocampal slices removed 1 hour after hypoxic seizures; this enhanced excitability in AMPARs resembles the modifications in synaptic efficacy observed in hippocampal LTP (Collingridge et al., 2004; Nicoll and Malenka, 1999), In models of LTP, similar rapid changes in synaptic potentiation are mediated by trafficking and endocytosis of AMPARs (Ehlers, 2000; Derkach et al., 2007). Neonatal seizures also lead to an enhancement of AMPAR-mediated minimally evoked unitary EPSCs and synaptic potency; similar enhanced AMPAR function is proposed as direct evidence for postsynaptic modification of AMPARs in LTP (Pratt et al., 2003; Isaac et al., 1996). Here, paired-pulse facilitation was not influenced following hypoxic seizures, suggesting the involvement of post-synaptic mechanisms. The increase in mEPSC frequency observed in hippocampal slices from animals experiencing hypoxic seizures also may reflect a reduction in the number of "silent synapses" and their conversion into functional AMPAR-containing synapses (Petralia et al., 1999). The early alterations resulting in hyperexcitability of hippocampal networks occur rapidly following seizure activity, and represents the early and rapid transition from normal to epileptic networks.

Coincident with the rapid enhancement of synaptic efficacy observed in the hippocampus following hypoxic seizures, we observed post-translational modifications of AMPAR subunits consistent with those reported in models of LTP (Lee et al., 2000). Phosphorylation of GluR15831 and GluR15845 was increased in hippocampi of rat pups as early as 1 hour after experiencing hypoxic seizures in vivo. GluR1 subunit-containing heteromeric receptors have been shown to be delivered into synapses during LTP following phosphorylation of the GluR1 receptor subunit (Song and Huganir, 2002), and these modifications influence bidirectional changes in efficacy of synaptic transmission (Lee et al., 2000; Matsuda et al., 1999). Phosphorylation of GluR15831 has been shown to increase single channel conductance in GluR1 subunit-containing AMPAR heteromers (Derkach et al., 1999; Mammen et al., 1997). Phosphorylation of GluR1 S845 has been reported to be critical for increased open-channel probability and activity-dependent insertion of GluR1-containing receptors into the membrane-associated pool of AMPARs (Esteban et al., 2003; Man et al., 2007; Oh et al., 2006), thereby modulating bidirectional synaptic plasticity. Furthermore, transgenic mice with mutations in these phosphorylation sites exhibit impaired LTP and spatial memory (Lee et al., 2003; Hu et al., 2007). Hence, phosphorylation of GluR15831 and S845 subunit enhance AMPAR EPSCs as seen here.

We also observed a rapid seizure-induced increase in phosphorylation of GluR25880. Previous reports have shown that dynamic regulatory mechanisms modulate the GluR2 phosphorylation and its subsequent interaction with synaptic proteins like GRIP1/2, ABP and PICK1 that promote internalization from the synaptic surface (Chung et al., 2000; Seidenman et al., 2003). Neonatal seizures induce phosphorylation of GluR25880 that in turn may cause GluR2 subunit internalization, suggested by the rapid increase in the inward rectification ratio of AMPAR currents following hypoxic seizures. This seizure-induced decrease in GluR2 would accentuate the existing preponderance of $Ca^{2+}$ permeable AMPARs in the immature brain (Kumar et al., 2002; Sanchez et al., 2001; Talos et al., 2006a; Talos et al., 2006b). In the immature brain, the $Ca^{2+}$ permeable heteromeric AMPARs may act as source of synaptically mediated $Ca^{2+}$ influx (Sanchez et al., 2001) in addition to that mediated by NMDARs (Malenka and Nicoll, 1993; Malenka and Bear, 2004).

The present work has identified a novel and critical role for AMPAR modifications that begins within hours following neonatal seizures and may represent the early mediators of the epileptogenic cascade. Cellular and molecular mechanisms previously associated with physiological synaptogenesis and synaptic plasticity may be co-opted by seizures for creation of hyperexcitable epileptogenic circuits. Our results indicate that hypoxic seizures induce $Ca^{2+}$ influx and mediate the rapid increase in the activity of protein kinases CaMKII, PKA and PKC in the hippocampal neurons, which in turn can lead to enhanced phosphorylation of the GluR1 and GluR2 receptor subunits. AMPAR receptor subunit phosphorylation can promote enhanced excitability and synaptic potentiation in hippocampal networks, thus initiating a persistent loop of enhanced AMPAR function and neuronal dysplasticity, which provides a target for intervention, such as with AMPAR antagonists. This unique dysplasticity may underlie the severe consequences of early-life seizures, including enhanced epileptogenesis observed in neonates as well as later impairment in cognitive function (Mikati et al., 2005; Silverstein and Jensen, 2007).

Post-Seizure Attenuation of AMPAR Potentiation and Enhanced Kinase Activity

A second major and novel finding is that seizure-induced alterations of the AMPAR and kinases can be attenuated or reversed even after the onset of the pathologic trigger. Post-treatment with the AMPAR antagonists NBQX, topiramate or the specific AMPAR antagonist GYKI-53773, blocked the acute and subacute enhancement in AMPAR EPSCs, GluR1 subunit phosphorylation and PKA, CaMKII and PKC activation observed following hypoxia-induced seizures, when administered during the early period after seizure induction. NBQX can block both AMPAR and KA receptors but preferentially blocks AMPARs. Topiramate is a non-competitive AMPAR antagonist with actions at other ligand-gated channels and GYKI-53773 specific noncompetitive AMPAR antagonist. Importantly, they share a common action of being able to block AMPAR-mediated neurotransmission. Here we show AMPAR antagonists reverse seizure-induced potentiation, and that activation of AMPARs, which are predominantly $Ca^{2+}$ permeable at this age (Silverstein and Jensen, 2007; Talos et al., 2006a; Talos et al., 2006b; Kumar et al., 2002; Sanchez et al., 2001) can be responsible for activating PKA, PKC and CaMKII as observed in this work.

Post-seizure treatment with NBQX or topiramate within the first 48 hours following hypoxic seizures prevents the long-term increase in susceptibility to seizures and seizure-induced neuronal injury (Koh et al., 2004). In the present work, the same post-seizure treatments that result in attenuation of the physiological alterations and subunit phosphorylation also resulted in prevention from enhanced seizure susceptibility at the level of the whole animal. We observed that rats post-treated with the AMPAR antagonist NBQX demonstrated a reversal of the increased seizure susceptibility in vivo at 72 hours post-hypoxic seizures, demonstrating an in vivo correlate to the reversal of the cellular changes observed in vitro.

Implications of AMPAR Potentiation for Intervention in the Epileptogenic Process Our work with pharmacological inhibition in vivo indicates that AMPARs can play an important role in the epileptogenic process, either directly or indirectly, by their effects on synaptic plasticity. While early life seizures promote epileptogenesis, repeated neonatal seizures have been shown to lead to long-term impairment of neurobehavior, cognition, and memory (Holmes et al., 1999; Sogawa et al., 2001; Silverstein and Jensen, 2007; Chen et al., 1999). The specific alterations in AMPAR function, GluR1 and GluR2 phosphorylation observed here may not only be associated with epileptogenesis, but also may produce impairment of normal network plasticity leading to deficits in neurobehavior and cognition. Similar activity-mediated alterations in AMPAR phosphorylation state and function have been reported to be involved in physiological phenomena such as LTP and LTD (Song and Huganir, 2002; Boehm and Malinow, 2005) and also in pathological settings including the stress response as well as addiction (Self and Choi, 2004; Carlezon, Jr. and Nestler, 2002; Saal et al., 2003; Dong et al., 2004; Xiang and Tietz, 2007; Kauer and Malenka, 2007).

Given the importance of AMPAR-mediated neurotransmission in both health and disease, the clinical use of AMPAR antagonists can provide significant improvement in neurological dysfunction. Significantly, the threshold for memory impairment with topiramate in healthy volunteers and patients with epilepsy is lower than lamotrigine and valproate, which are currently clinically used as anti-convulsants (Meador et al., 2003; Meador et al., 2005). In light of our results, the memory impairments reported with topiramate may in part be due to its action on AMPAR synapses in hippocampus. On the other hand, more preliminary human studies with the administration of specific AMPAR antagonist GYKI-53773, which has been used in this work, show less cognitive impairment (Howes and Bell, 2007; Chappell et al., 2002).

The efficacy of AMPAR antagonists in attenuating epileptogenesis, especially when administered following neonatal seizures, can be particularly useful clinically given their relative safety profile and lack of apoptotic cell death induction at pharmacologically tolerated doses in the developing brain (Bittigau et al., 2002; Ikonomidou et al., 1999). Conventional agents like phenyloin and barbiturates, that currently constitute the first line of therapy, lack efficacy for acute seizure suppression in almost 50% of infants with neonatal seizures and have no effect on long-term outcome (Painter et al., 1999; Sankar and Painter, 2005). AMPAR antagonists, even when administered after seizure onset, provide an effective age-specific therapeutic strategy that should have a role in preventing epileptogenesis and epilepsy-related cognitive impairment.

REFERENCES

1. Barria A, Derkach V, Soderling T (1997) Identification of the $Ca^{2+}$/calmodulin-dependent protein kinase II regulatory phosphorylation site in the alpha-amino-3-hydroxyl-5-methyl-4-isoxazole-propionate-type glutamate receptor. J Biol Chem 272: 32727-32730.
2. Ben Ari Y, Holmes G L (2006) Effects of seizures on developmental processes in the immature brain. Lancet Neurol 5: 1055-1063.
3. Bittigau P, Sifringer M, Genz K, Reith E, Pospischil D, Govindarajalu S, Dzietko M, Pesditschek S, Mai I, Dikranian K, Olney J W, Ikonomidou C (2002) Antiepileptic drugs and apoptotic neurodegeneration in the developing brain. Proc Natl Acad Sci USA 99: 15089-15094.
4. Boehm J, Malinow R (2005) AMPA receptor phosphorylation during synaptic plasticity. Biochem Soc Trans 33: 1354-1356.
5. Carlezon W A, Jr., Nestler E J (2002) Elevated levels of GluR1 in the midbrain: a trigger for sensitization to drugs of abuse? Trends Neurosci 25: 610-615.
6. Chappell A S, Sander J W, Brodie M J, Chadwick D, Lledo A, Zhang D, Bjerke J, Kiesler G M, Arroyo S (2002) A crossover, add-on trial of talampanel in patients with refractory partial seizures. Neurology 58: 1680-1682.
7. Chen K, Baram T Z, Soltesz I (1999) Febrile seizures in the developing brain result in persistent modification of neuronal excitability in limbic circuits. Nature Medicine 5: 888-894.
8. Chung H J, Xia J, Scannevin R H, Zhang X, Huganir R L (2000) Phosphorylation of the AMPA receptor subunit GluR2 differentially regulates its interaction with PDZ domain-containing proteins. J Neurosci 20: 7258-7267.
9. Collingridge G L, Isaac J T, Wang Y T (2004) Receptor trafficking and synaptic plasticity. Nat Rev Neurosci 5: 952-962.
10. Cornejo B J, Mesches M H, Coultrap S, Browning M D, Benke T A (2007) A single episode of neonatal seizures permanently alters glutamatergic synapses. Ann Neurol 61: 411-426.
11. Derkach V, Barria A, Soderling T R (1999) $Ca^{2+}$/calmodulin-kinase II enhances channel conductance of alpha-amino-3-hydroxy-5-methyl-4-isoxazolepropionate type glutamate receptors. Proc Natl Acad Sci USA 96: 3269-3274.
12. Derkach V A, Oh M C, Guire E S, Soderling T R (2007) Regulatory mechanisms of AMPA receptors in synaptic plasticity. Nat Rev Neurosci 8: 101-113.
13. Doherty J, Dingledine R (2002) The roles of metabotropic glutamate receptors in seizures and epilepsy. Curr Drug Targets CNS Neurol Disord 1: 251-260.
14. Dong Y, Saal D, Thomas M, Faust R, Bonci A, Robinson T, Malenka R C (2004) Cocaine-induced potentiation of synaptic strength in dopamine neurons: behavioral correlates in GluRA(-/-) mice. Proc Natl Acad Sci USA 101: 14282-14287.
15. Durand G M, Zukin R S (1993) Developmental regulation of RNAs encoding rat brain kainate/AMPA receptors: A northern analysis study. Journal of Neurochemistry 61: 2239-2246.
16. Dzhala V I, Talos D M, Sdrulla D A, Brumback A C, Mathews G C, Benke T A, Delpire E, Jensen F E, Staley K J (2005) NKCC1 transporter facilitates seizures in the developing brain. Nat Med 11: 1205-1213.
17. Ehlers M D (2000) Reinsertion or degradation of AMPA receptors determined by activity-dependent endocytic sorting. Neuron 28: 511-525.
18. Esteban J A, Shi S H, Wilson C, Nuriya M, Huganir R L, Malinow R (2003) PKA phosphorylation of AMPA receptor subunits controls synaptic trafficking underlying plasticity. Nat Neurosci 6: 136-143.
19. Hayashi Y, Shi S H, Esteban J A, Piccini A, Poncer J C, Malinow R (2000) Driving AMPA receptors into synapses by LTP and CaMKII: requirement for GluR1 and PDZ domain interaction. Science 287: 2262-2267.
20. Holmes G L, Sarkisian M, Ben-Ari Y, Chevassus-Au-Louis N (1999) Mossy fiber sprouting after recurrent seizures during early development in rats. Journal of Comparative Neurology 404(4): 537-553.
21. Howes J F, Bell C (2007) Talampanel. Neurotherapeutics 4: 126-129.
22. Hu H, Real E, Takamiya K, Kang M G, Ledoux J, Huganir R L, Malinow R (2007) Emotion enhances learning via norepinephrine regulation of AMPA-receptor trafficking. Cell 131: 160-173.
23. Ikonomidou C, Bosch F, Miksa M, Bittigau P, Vockler J, Dikranian K, Tenkova T, Stefovska V, Turski L, Olney J W (1999) Blockade of NMDA receptors and apoptotic neurodegeneration in the developing brain. Science 283: 70-74.
24. Isaac J T, Hjelmstad G O, Nicoll R A, Malenka R C (1996) Long-term potentiation at single fiber inputs to hippocampal CA1 pyramidal cells. Proc Natl Acad Sci USA 93: 8710-8715.
25. Jensen F E (2006) Developmental factors regulating susceptibility to perinatal brain injury and seizures. Current Opin Pediatr 18: 628-633.
26. Jensen F E, Applegate C D, Holtzman D, Bolin T, Burchfiel J (1991) Epileptogenic effect of hypoxia in the immature rodent brain. Ann of Neurol 29: 629-637.

27. Jensen F E, Holmes G L, Lombroso C T, Blume H K, Firkusny I R (1992) Age dependent changes in long term seizure susceptibility and behavior after hypoxia in rats. Epilepsia 33: 971-980.
28. Jensen F E, Wang C, Stafstrom C E, Liu Z, Geary C, Stevens M C (1998) Acute and chronic increases in excitability in rat hippocampal slices after perinatal hypoxia in vivo. Neurophysiol 79: 73-81.
29. Kameyama K, Lee H K, Bear M F, Huganir R L (1998) Involvement of a postsynaptic protein kinase A substrate in the expression of homosynaptic long-term depression. Neuron 21: 1163-1175.
30. Kapus G, Szekely J I, Durand J, Ruiz A, Tamawa I (2000) AMPA receptor antagonists, GYKI 52466 and NBQX, do not block the induction of long-term potentiation at therapeutically relevant concentrations. Brain Res Bull 52: 511-517.
31. Kauer J A, Malenka R C (2007) Synaptic plasticity and addiction. Nat Rev Neurosci 8: 844-858.
32. Kim C H, Chung H J, Lee H K, Huganir R L (2001) Interaction of the AMPA receptor subunit GluR2/3 with PDZ domains regulates hippocampal long-term depression. Proc Natl Acad Sci USA 98: 11725-11730.
33. Koh S, Tibayan F D, Simpson J, Jensen F E (2004) NBQX or topiramate treatment following perinatal hypoxia-induced seizures prevents later increases in seizure-induced neuronal injury. Epilepsia 45: 569-575.
34. Kumar S S, Bacci A, Kharazia V, Huguenard J R (2002) A developmental switch of AMPA receptor subunits in neocortical pyramidal neurons. J Neurosci 22: 3005-3015.
35. Lee H K, Barbarosie M, Kameyama K, Bear M F, Huganir R L (2000) Regulation of distinct AMPA receptor phosphorylation sites during bidirectional synaptic plasticity. Nature 405: 955-959.
36. Lee H K, Takamiya K, Han J S, Man H, Kim C H, Rumbaugh G, Yu S, Ding L, He C, Petralia R S, Wenthold R J, Gallagher M, Huganir R L (2003) Phosphorylation of the AMPA receptor GluR1 subunit is required for synaptic plasticity and retention of spatial memory. Cell 112: 631-643.
37. Malenka R C, Bear M F (2004) LTP and LTD: an embarrassment of riches. Neuron 44: 5-21.
38. Malenka R C, Nicoll R A (1993) NMDA-receptor-dependent synaptic plasticity: multiple forms and mechanisms. Trends in Neurosciences 16(12): 521-527.
39. Malinow R, Malenka R C (2002) AMPA receptor trafficking and synaptic plasticity. Annu Rev Neurosci 25: 103-126.
40. Mammen A L, Kameyama K, Roche K W, Huganir R L (1997) Phosphorylation of the alpha-amino-3-hydroxy-5-methylisoxazole4-propionic acid receptor GluR1 subunit by calcium/calmodulin-dependent kinase II. J Biol Chem 272: 32528-32533.
41. Man H-Y, Sekine Y, Huganir R (2007) Regulation of α-amino-3-hydroxy-5-methyl-4-isoxazolepropionic acid receptor trafficking through PKA phosphorylation of the Glu receptor 1 subunit. PNAS 104: 3579-3584.
42. Matsuda S, Mikawa S, Hirai H (1999) Phosphorylation of serine-880 in GluR2 by protein kinase C prevents its C terminus from binding with glutamate receptor-interacting protein. J Neurochem 73: 1765-1768.
43. McCormack S G, Stometta R L, Zhu J J (2006) Synaptic AMPA receptor exchange maintains bidirectional plasticity. Neuron 50: 75-88.
44. McNamara J O, Huang Y Z, Leonard A S (2006) Molecular signaling mechanisms underlying epileptogenesis. Sci STKE 2006: re12.
45. Meador K J, Loring D W, Hulihan J F, Kamin M, Karim R (2003) Differential cognitive and behavioral effects of topiramate and valproate. Neurology 60: 1483-1488.
46. Meador K J, Loring D W, Vahle V J, Ray P G, Werz M A, Fessler A J, Ogrocki P, Schoenberg M R, Miller J M, Kustra R P (2005) Cognitive and behavioral effects of lamotrigine and topiramate in healthy volunteers. Neurology 64: 2108-2114.
47. Mikati M A, Zeinieh M P, Kurdi R M, Harb S A, El Hokayem J A, Daderian R H, Shamseddine A, Obeid M, Bitar F F, El Sabban M (2005) Long-term effects of acute and of chronic hypoxia on behavior and on hippocampal histology in the developing brain. Brain Res Dev Brain Res 157: 98-102.
48. Nicoll R A, Malenka R C (1999) Expression mechanisms underlying NMDA receptor-dependent long-term potentiation. Ann NY Acad Sci 868: 515-525.
49. Noebels J L (2003) The biology of epilepsy genes. Annu Rev Neurosci 26: 599-625.
50. Oh M C, Derkach V A, Guire E S, Soderling T R (2006) Extrasynaptic membrane trafficking regulated by GluR1 serine 845 phosphorylation primes AMPA receptors for long-term potentiation. J Biol Chem 281: 752-758.
51. Painter M J, Scher M S, Stein A D, Armatti S, Wang Z, Gardiner J C, Paneth N, Minnigh B, Alvin J (1999) Phenobarbital compared with phenyloin for the treatment of neonatal seizures. N Engl J Med 341: 485-489.
52. Petralia R S, Esteban J A, Wang Y X, Partridge J G, Zhao H M, Wenthold R J, Malinow R (1999) Selective acquisition of AMPA receptors over postnatal development suggests a molecular basis for silent synapses. Nat Neurosci 2: 31-36.
53. Pratt K G, Watt A J, Griffith L C, Nelson S B, Turrigiano G G (2003) Activity-dependent remodeling of presynaptic inputs by postsynaptic expression of activated CaMKII. Neuron 39: 269-281.
54. Raastad M (1995) Extracellular activation of unitary excitatory synapses between hippocampal CA3 and CA1 pyramidal cells. Eur J Neurosci 7: 1882-1888.
55. Rakic P, Bourgeois J P, Eckenhoff M F, Zecevic N, Goldman-Rakic P S (1989) Concurrent overproduction of synapses in diverse regions of primate cortex. Science 232: 232-235.
56. Raol Y H, Lund I V, Bandyopadhyay S, Zhang G, Roberts D S, Wolfe J H, Russek S J, Brooks-Kayal A R (2006) Enhancing GABA(A) receptor alpha 1 subunit levels in hippocampal dentate gyms inhibits epilepsy development in an animal model of temporal lobe epilepsy. J Neurosci 26: 11342-11346.
57. Saal D, Dong Y, Bonci A, Malenka R C (2003) Drugs of abuse and stress trigger a common synaptic adaptation in dopamine neurons. Neuron 37: 577-582.
58. Sanchez R M, Dai W, Levada R E, Lippman J J, Jensen F E (2005) AMPA/kainate receptor-mediated downregulation of GABAergic synaptic transmission by calcineurin after seizures in the developing rat brain. J Neurosci 25: 3442-3451.
59. Sanchez R M, Koh S, Rio C, Wang C, Lamperti E D, Sharma D, Corfas G, Jensen F E (2001) Decreased glutamate receptor 2 expression and enhanced epileptogenesis in immature rat hippocampus after perinatal hypoxia-induced seizures. J Neurosci 21: 8154-8163.
60. Sankar R, Painter M J (2005) Neonatal seizures: after all these years we still love what doesn't work. Neurology 64: 776-777.
61. Seidenman K J, Steinberg J P, Huganir R, Malinow R (2003) Glutamate receptor subunit 2 Serine 880 phosphorylation modulates synaptic transmission and mediates plasticity in CA1 pyramidal cells. J Neurosci 23: 9220-9228.
62. Self D W, Choi K H (2004) Extinction-induced neuroplasticity attenuates stress-induced cocaine seeking: a state-dependent learning hypothesis. Stress 7: 145-155.
63. Silverstein F S, Jensen F E (2007) Neonatal seizures. Ann Neurol 62: 112-120.
64. Sogawa Y, Monokoshi M, Silveira D C, Cha B H, Cilio M R, McCabe B K, Liu X, Hu Y, Holmes G L (2001) Timing of cognitive deficits following neonatal seizures: relationship to histological changes in the hippocampus. Brain Res Dev Brain Res 131: 73-83.
65. Song I, Huganir R L (2002) Regulation of AMPA receptors during synaptic plasticity. Trends Neurosci 25: 578-588.
66. Sutula T, Koch J, Golarai G, Watanabe Y, McNamara J O (1996) NMDA receptor dependence of kindling and mossy fiber sprouting: evidence that the NMDA receptor regulates patterning of hippocampal circuits in the adult brain. J Neurosci 16: 7398-7406.
67. Talos D M, Fishman R E, Park H, Folkerth R D, Follett P L, Volpe J J, Jensen F E (2006a) Developmental regulation of alpha-amino-3-hydroxy-5-methyl-4-isoxazole-propionic acid receptor subunit expression in forebrain and relationship to regional susceptibility to hypoxic/ischemic injury. I. Rodent cerebral white matter and cortex. J Comp Neurol 497: 42-60.
68. Talos D M, Follett P L, Folkerth R D, Fishman R E, Trachtenberg F L, Volpe J J, Jensen F E (2006b) Developmental regulation of alpha-amino-3-hydroxy-5-methyl-4-isoxazole-propionic acid receptor subunit expression in forebrain and relationship to regional susceptibility to hypoxic/ischemic injury. II. Human cerebral white matter and cortex. J Comp Neurol 497: 61-77.
69. Volpe J J (2001) Neurology of the Newborn. Philadelphia: Saunders.
70. Wenthold R J, Yokotani N, Doi K, Wada K (1992) Immunochemical characterization of the non-NMDA glutamate receptor using subunit-specific antibodies. The Journal of Biological Chemistry 267(1): 501-507.
71. Wyllie D J, Manabe T, Nicoll R A (1994) A Rise in Postsynaptic $Ca^{2+}$ Potentiates Miniature Excitatory Postsynaptic Currents and AMPA Responses in Hippocampal Neurons. Neuron 12: 127-138.
72. Wyllie D J, Nicoll R A (1994) A role for protein kinases and phosphatases in the Ca(2+)-induced enhancement of hippocampal AMPA receptor-mediated synaptic responses. Neuron 13: 635-643.
73. Wyszynski M, Valtschanoff J G, Naisbitt S, Dunah A W, Kim E, Standaert D G, Weinberg R, Sheng M (1999) Association of AMPA receptors with a subset of glutamate receptor-interacting protein in vivo. J Neurosci 19: 6528-6537.
74. Xiang K, Tietz E I (2007) Benzodiazepine-induced hippocampal CA1 neuron alpha-amino-3-hydroxy-5-methyl-isoxasole-4-propionic acid (AMPA) receptor plasticity linked to severity of withdrawal anxiety: differential role of voltage-gated calcium channels and N-methyl-D-aspartic acid receptors. Behav Pharmacol 18: 447-460.

The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims

What is claimed is:
1. A therapeutic method for treating a patient post-seizure comprising administering to the patient NBQX (2,3-dihydroxy-6-nitro-7-sulfamoyl-benzo[f]quinoxaline-2,3-dione), KN-62 (1-[N,O-bis(5-isoquinolinesulfonyl)-N-methyl-L-tyrosyl]-4-phenylpiperazine), and rapamycin.
2. The method of claim 1, further comprising administering to the patient epithalon, a corticosteroid, or a non-steroidal anti-inflammatory drug (NSAID).
3. The method of claim 2, wherein NBQX, KN-62, rapamycin, and the corticosteroid or NSAID are administered sequentially,
wherein NBQX is administered first, within 24 hours post-seizure, the KN-62 is administered second, within 48 hours post-seizure, rapamycin is administered third, within 96 hours post-seizure, and the corticosteroid or NSAID is administered fourth, within 96 hours post-seizure.
4. The method of claim 1, wherein NBQX, KN-62, and rapamycin are administered sequentially, wherein NBQX is administered first, within 24 hours post-seizure, KN-62 is administered second, within 48 hours post-seizure, and rapamycin is administered third, within 96 hours post-seizure.

* * * * *

UNITED STATES PATENT AND TRADEMARK OFFICE
CERTIFICATE OF CORRECTION

PATENT NO. : 8,785,446 B2  
APPLICATION NO. : 12/688892  
DATED : July 22, 2014  
INVENTOR(S) : Frances E. Jensen and Sanjay N. Rakhade Page 1 of 1

It is certified that error appears in the above-identified patent and that said Letters Patent is hereby corrected as shown below:

In the Specification

Column 1, line 5, delete "DP10D00347" and insert -- DP1 OD003347 --

Signed and Sealed this
Twenty-fifth Day of November, 2014

Michelle K. Lee
*Deputy Director of the United States Patent and Trademark Office*